US011311393B2

(12) United States Patent
Sampson et al.

(10) Patent No.: US 11,311,393 B2
(45) Date of Patent: Apr. 26, 2022

(54) UNIVERSAL DIGIT

(71) Applicant: DBM, LLC, Rochester, MN (US)

(72) Inventors: Brandon Sampson, Pine Island, MN (US); Marty Frana, Rochester, MN (US)

(73) Assignee: DBM, LLC, Rochester, MN (US)

( * ) Notice: Subject to any disclaimer, the term of this patent is extended or adjusted under 35 U.S.C. 154(b) by 0 days.

(21) Appl. No.: 16/637,159

(22) PCT Filed: Aug. 6, 2018

(86) PCT No.: PCT/US2018/045452
§ 371 (c)(1),
(2) Date: Feb. 6, 2020

(87) PCT Pub. No.: WO2019/032478
PCT Pub. Date: Feb. 14, 2019

(65) Prior Publication Data
US 2020/0360157 A1 Nov. 19, 2020

Related U.S. Application Data

(60) Provisional application No. 62/541,743, filed on Aug. 6, 2017.

(51) Int. Cl.
*A61F 2/58* (2006.01)
*A61F 2/68* (2006.01)

(52) U.S. Cl.
CPC ............. *A61F 2/586* (2013.01); *A61F 2/68* (2013.01); *A61F 2002/6836* (2013.01); *A61F 2002/6854* (2013.01)

(58) Field of Classification Search
CPC .... A61F 2/586; A61F 2/58; A61F 2/68; A61F 2002/6836; A61F 2002/6854
See application file for complete search history.

(56) References Cited

U.S. PATENT DOCUMENTS

| 2,568,299 A * | 9/1951 | Philpott | A61F 2/586 |
| | | | 623/64 |
| 6,908,489 B2 * | 6/2005 | Didrick | A61F 2/586 |
| | | | 623/64 |

(Continued)

FOREIGN PATENT DOCUMENTS

| DE | 294453 | * | 4/1915 |
| DE | 102012003360 A1 | | 8/2013 |

(Continued)

OTHER PUBLICATIONS

"International Search Report", Application No. PCT/US2018/045452, dated Oct. 24, 2018, 1.

(Continued)

*Primary Examiner* — Bruce E Snow
(74) *Attorney, Agent, or Firm* — Todd R. Fronek; Larkin Hoffman Daly & Lindgren, Ltd.

(57) ABSTRACT

A universal digit is formed to be attachable to the residual digit of a patient, and to have a lockable joint, so as to provide considerable utility and flexibility. The structure of the joint member allows the universal digit to be easily adjusted and manipulated so that the extension portion can be locked into multiple positions by easily manipulating adjustment buttons. The extension is rotatable about a first longitudinal axis, and is further rotatable about a transverse axis which is perpendicular to the longitudinal axis. The joint structure thus has three dimensions of movement and provides a significant number of diverse options for positioning of the extension. Unique locking mechanisms within the various structures allow the universal digit to be rigidly held in the desired position, thereby increasing the utility for a patient/user.

17 Claims, 4 Drawing Sheets

(56) References Cited

U.S. PATENT DOCUMENTS

| | | | |
|---|---|---|---|
| 8,052,760 B2 | 11/2011 | Egilsson et al. | |
| 8,097,043 B2 | 1/2012 | Egilsson | |
| 9,320,621 B2* | 4/2016 | Iversen | A61F 2/583 |
| 9,629,731 B2 | 4/2017 | Thompson et al. | |
| 10,271,966 B2* | 4/2019 | Glasgow | A61F 2/586 |
| 2012/0330432 A1 | 12/2012 | Fong | |
| 2013/0197671 A1* | 8/2013 | Johannes | A61F 2/72 |
| | | | 623/64 |
| 2014/0114436 A1 | 4/2014 | Tresco et al. | |
| 2014/0114439 A1* | 4/2014 | Iversen | A61F 2/70 |
| | | | 623/64 |
| 2015/0052993 A1 | 2/2015 | Batzdorff | |
| 2016/0166409 A1 | 6/2016 | Goldfarb et al. | |
| 2016/0367383 A1 | 12/2016 | Sensinger et al. | |
| 2020/0155330 A1* | 5/2020 | Segil | A61F 2/72 |

FOREIGN PATENT DOCUMENTS

| | | | |
|---|---|---|---|
| DE | 102014011554 A1 | | 2/2016 |
| GB | 345340 | * | 3/1931 |

OTHER PUBLICATIONS

"Partial Hand Solutions, LLC—Products", website, http://www.partialhandsolutions.com/products/, 2019, 8 pages.

* cited by examiner

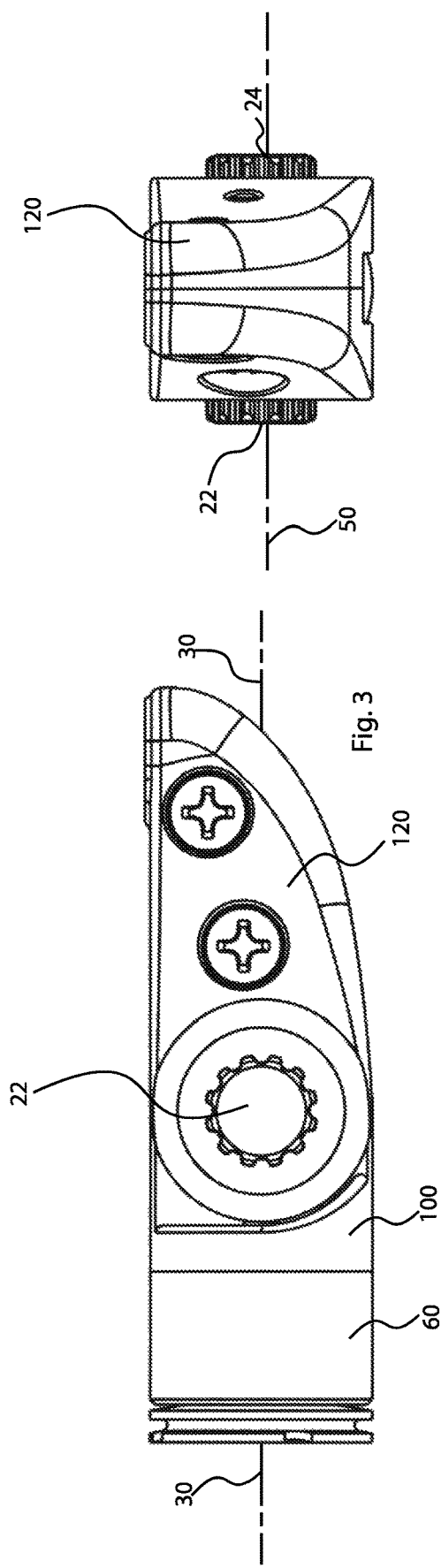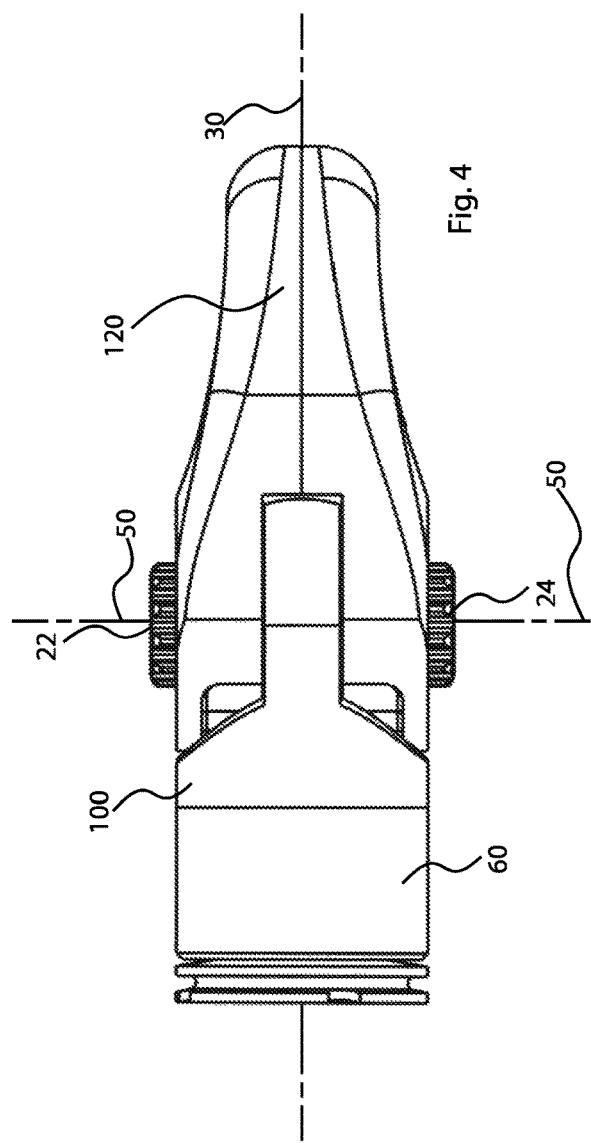

UNIVERSAL DIGIT

BACKGROUND

In the field of prosthetics, there is a continual need to provide solutions for patients of all types. In those situations where patients have lost a digit, at the MP Joint, or below, it is beneficial to provide a universal digit capable of enabling that particular patient to carry out and complete multiple tasks. Due to the loss involved it is beneficial to have a joint of some type be included in the prosthetic digit. Current approaches typically include joints which are either motorized, or manually repositionable. As anticipated, motorized joints typically involve actuators and robotics of some type. That said, these systems can be complex and expensive. This cost and complexity can often times make fitting and or use impossible or impractical. In prosthetics having manually repositionable joints, a friction joint is typically involved. As is recognized, those joints are held in place by certain designed-in levels of friction, and are moved by manually overcoming this friction. This approach is often undesirable however, since the patient's needs and applications can vary greatly, with varied levels of friction being appropriate for each application. In the end, this makes these joints somewhat impractical and not usable.

In the case of frictionally positional digits, several additional complications arise when used. Specifically, the desired level of friction and forces involved can never be appropriate for all situations. In some cases undo levels of force are required making them impractical to reposition. In other situations, the frictional forces require to reposition cannot be high enough. In these cases, use becomes impractical since the digit will adjust its configuration when being used. As such, the current offerings are impractical and not optimal in many situations.

SUMMARY

In order to address ongoing needs, and provide a more effective prosthetic device, a universal digit is provided which includes a repositionable locking joint which can be easily positioned in multiple orientations. The universal digit has a barrel portion which is configured to be attached to a residual digit, and generally align therewith. An extension portion exists at an opposite end of the universal digit, which is coupled to the barrel portion by a central joint structure. Based upon internal structures, and appropriate locking mechanisms, the extension itself can be positioned in many different orientations with respect to the barrel portion. More specifically, the extension portion is rotatable about a central longitudinal axis (which is generally aligned with the barrel portion). In addition, the extension portion is rotatable about a transverse axis, with the transverse axis being perpendicular to the longitudinal axis. Since the central joint member is rotatable about the above-mentioned longitudinal axis, and the transverse axis also rotates in conjunction with this component, the universal digit has infinite positionability, and thus extreme utility for the user.

To provide the necessary locking structure, the central joint member includes a button-locking mechanism which can be operated by a user. To accomplish this, two cooperating buttons are depressed, thus allowing rotation about the transverse axis. When the extension portion is positioned in a predetermined orientation, the central joint member (and related extension portion) is also rotatable about the longitudinal axis. However, when the extension is not in this predetermined position, this portion of the central joint member is locked in place.

BRIEF DESCRIPTION OF THE DRAWINGS

Additional objects and advantages of the universal digit can be seen from reading the following detailed description in conjunction with the drawings in which:

FIG. 3 is a side view of the universal digit;

FIG. 4 is a bottom view of the universal digit;

FIG. 5 is a front view of the universal digit; and

DESCRIPTION OF THE EMBODIMENTS

As discussed below in further detail, the universal digit 10 of the illustrated embodiments is a prosthetic component which is capable of being adapted to many different situations. Depending on the patient's situation and/or needs, universal digit 10 can be used to replace any lost digit, and/or can also be used to replace multiple digits. As will be described in detail, universal digit 10 is adjustable in many different ways, including 360 degrees about a longitudinal axis, and approximately 180 to 220 degrees about a transverse axis. Further, universal digit 10 can be securely locked in position, once the desired orientation/configuration is determined. In this manner, a user is provided with a significant level of utility and flexibility.

Figure 1:
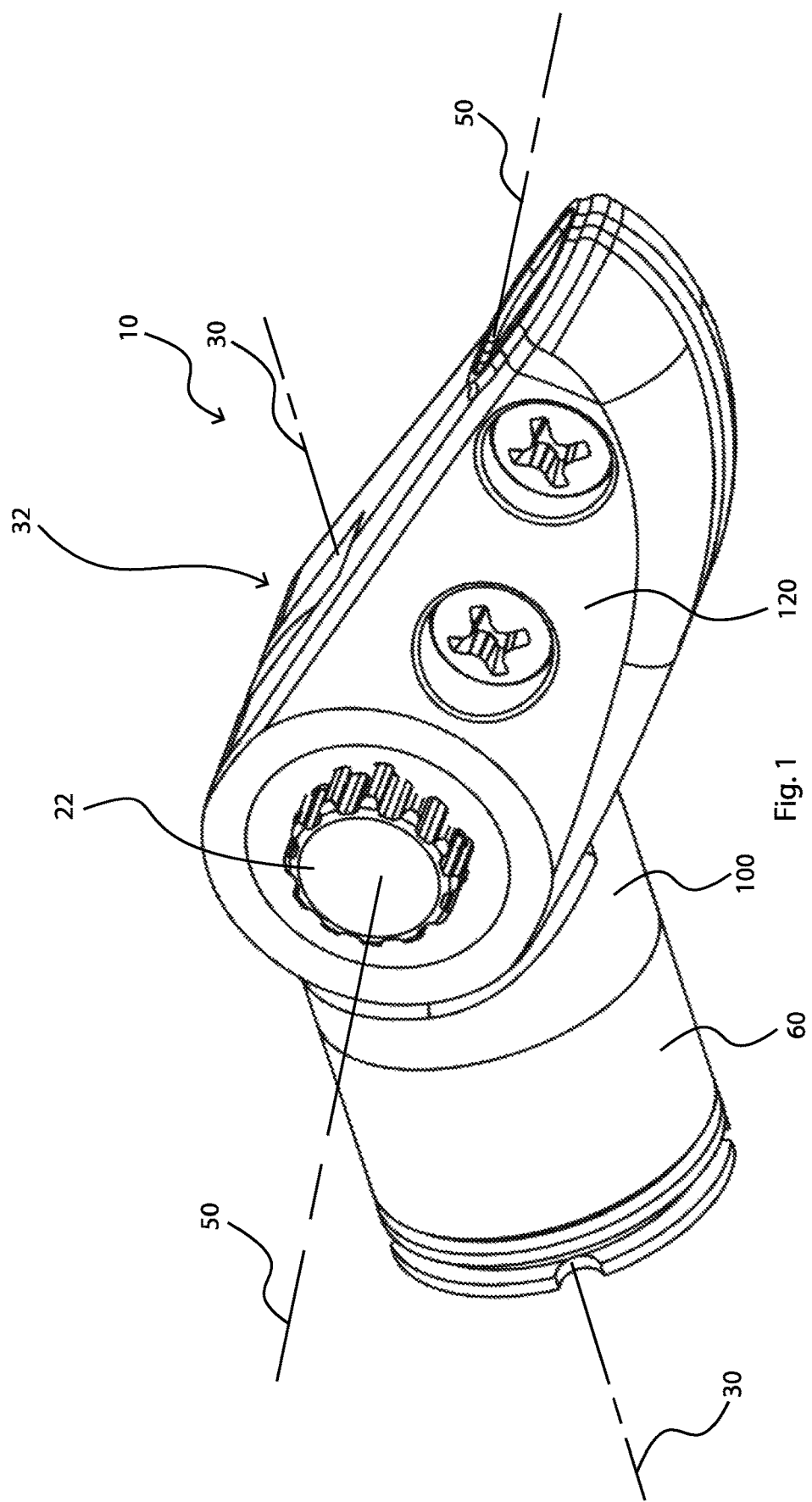
FIGS. 1 and 2 are perspective views of one embodiment of the universal digit.

Referring now to FIG. 1, a first perspective view of universal digit 10 is illustrated. As shown in FIG. 1, universal digit 10 is oriented in a first position, with an end or tip or extension portion 120 angled downwardly with respect to a barrel portion 60. As will be further discussed below, a hinge mechanism 30 allows for rotation of tip portion 120 about a transverse axis 50. Barrel portion 60 is generally cylindrical, having a central longitudinal axis 30. In use, barrel portion 60 will generally be attached to a user's hand, and will be aligned with a residual digit. Although variations are possible, it is generally contemplated that universal digit 10 can be used in conjunction with the loss of any digit, and will be deployed when the residual digit exists from just below the MP Joint or more proximal.

Figure 2:
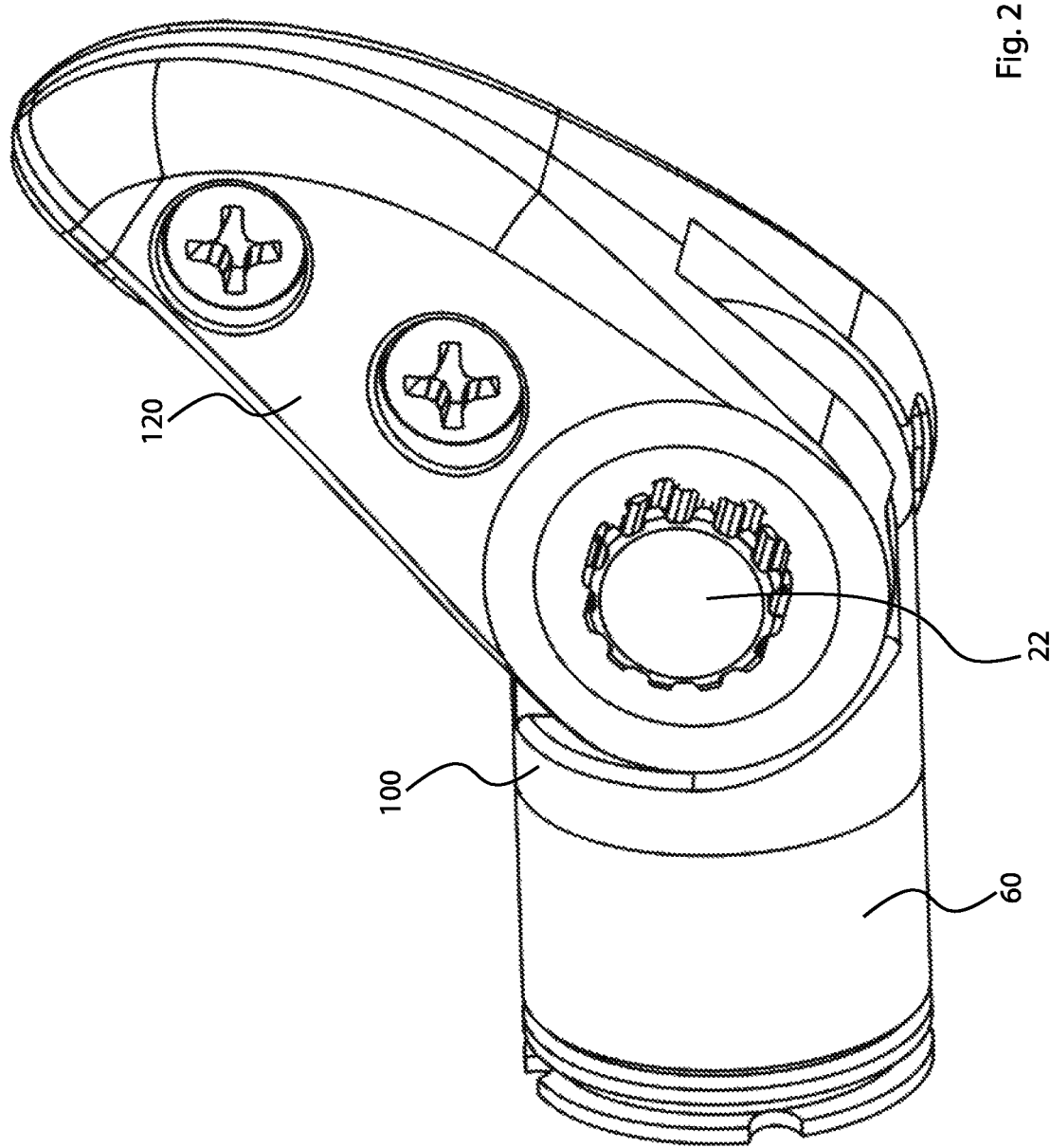

FIG. 2 shows an alternative perspective view of universal digit 10, with end or tip portion 120 positioned in an upward orientation. This simply provides one example of the adjustability provided by universal digit 10. For further insight, FIGS. 3-5 illustrate a side view, bottom view, and front view, respectively, of universal digit 10.

Figure 6:
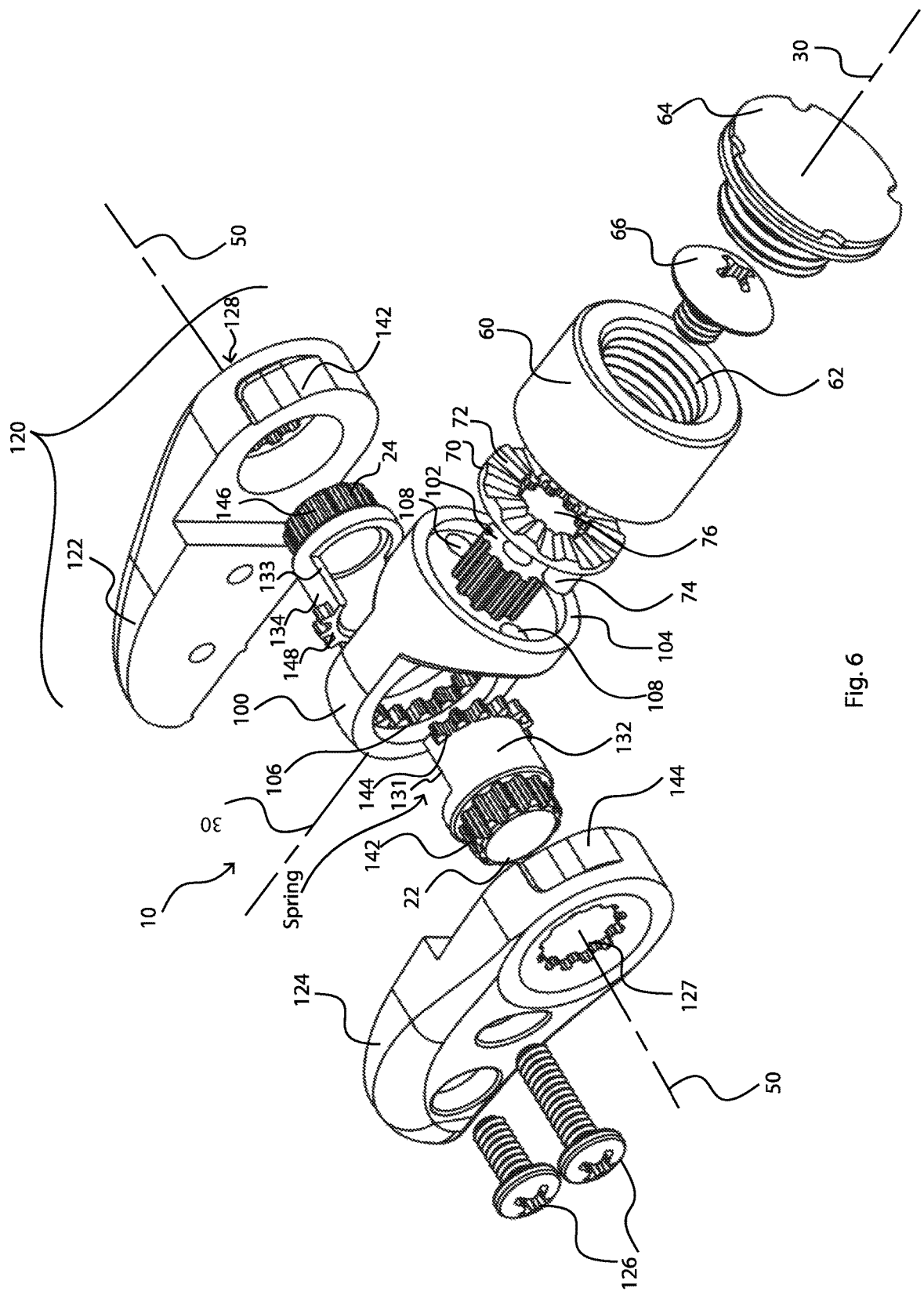
FIG. 6 is an exploded view of the universal digit.

Referring now to FIG. 6, an exploded view of universal digit 10 is illustrated. In this view, certain portions of the interior structures are illustrated, which helps to better explain the internal working/operation of universal digit 10. As will be recognized and appreciated, this particular embodiment has been uniquely designed and configured to allow universal digit 10 to be locked in multiple orientations, thus providing the above mentioned utility and versatility. Those skilled in the art will recognize that variations are possible and similar mechanisms could be utilized to achieve the specific features described.

Referring again to FIGS. 1-5, universal digit 10 includes a pair of cooperating buttons 22, 24. As will be further detailed below, pressing buttons 22 and 24 in an inward direction so they are in a depressed position, will allow for rotation of various components along the transverse axis discussed above. Specifically, pressing these buttons will allow for approximately 220 degrees of rotation about transverse axis 50 (although more travel could be achieved by modifying certain structures). Once buttons 22, 24 are released, they will move back to a released position thus causing the locking mechanisms to automatically return to an engaged orientation, and causing the universal digit to be locked in its desired configuration/orientation. As will also be discussed, using buttons 22 and 24 to position end portion 120 is a particular predetermined orientation or position, will also allow end portion 120 to be rotated a full 360 degrees about longitudinal axis 30.

Again, FIG. 6 illustrates an exploded view of universal digit 10 and allows several internal components and structures to be better seen. As generally mentioned above, universal digit 10 includes a barrel portion 60, which is cylindrical in nature and includes threads 62 which are configured for attachment to a common connection plate 64. Although threads are discussed above, other connection methodologies could be utilized. That said, common connection plate 64 is a well understood connection mechanism, universally used for prosthetics. The opposite side of barrel portion 60 includes a gear seat structure (not shown), which is specifically configured to interact with a slidable collar 70. Slidable collar 70 includes gears or teeth 72 extending from one side, and a pair of posts 74 extending from an opposite side. Further, slidable collar 70 is specifically configured to have a central aperture 76, with inwardly facing teeth or gears 78. As will be further discussed below, teeth or gears 78 and post 74 are specifically designed and configured to interact with other structures and to further accommodate operation. More specifically, slidable collar 70 is uniquely designed to be slidable along post 74, but will not rotate independently.

As also seen in FIG. 6, universal digit 10 includes a central joint member 100 which is uniquely designed to accommodate the functions and capabilities of the device. As seen, a bottom portion of central joint member 100 includes a toothed or geared post 102 having a general cylindrical shape. Extending inwardly from a bottom portion of gear post 102 is a bottom aperture 104 specifically designed to receive an attachment screw 66. When attached, gear post 102 will be held immediately adjacent to a related surface on an upper portion (not shown) of barrel portion or member 60. This connection will allow rotation of central joint member 100 with respect to barrel member 60 about longitudinal axis 30.

Central joint member 100 also has a pair of openings 108 within a recess 105, which are specifically configured to receive posts 74. As will be further discussed below, slidable collar 70 can be locked into various positions by utilizing forces applied to posts 74.

Universal digit 10 also includes a rotatable extension assembly 120 which is made up of a first extension half 122 and a second extension half 124. A pair of attachment screws 126 are utilized to join first extension half 122 and second extension half 124. As will be appreciated, extension assembly (when assembled) has a slot 125 at one end. As further discussed below, slot 125 will cooperate with central joint member to accommodate the desired functionality of universal digit 10. Also cooperating with first extension half 122 and second extension half 122, is a button mechanism made up of a first button half 132 and a second button half 134. More specifically, the button mechanism also provides a coupling mechanism to central joint member 100. First button half 132 will include first button 22 on one side, while second button half 134 will include second button 24 on an opposite side thereof.

As further outlined below, universal digit 10 has a very effective and efficient locking mechanism, which allows for locked positioning as desired by a user. Again, this locking mechanism is operated by activation of first button 22 and second button 24. That said, many structures cooperate with one another to allow this function to be carried out. As can be seen, first button half 132 includes a first gear structure 142 situated on an outward end and a second gear structure 144 situated on an inward end. Similarly, second button half 134 includes a first gear structure situated on an outward end 146 and a second gear structure 148 situated on an inward end. When assembled, first gear structure 142 will interact with a receiving aperture 127 within extension half 124 and second gear structure 146 of second button half 134 will be received in a similar aperture 128 in extension half 122. Both receiving apertures 127, 128 have cooperating teeth or gears on an inner edge surface which cooperate with gear structures 142, 146, thus insuring that button halves 132, 134 are slidable with respect to extension halves 122, 124, but are not allowed to rotate.

Although not shown, a spring will be used to urge first button half 132 and second button half 134 in an outward direction. For reference the location of the spring is noted in FIG. 6. First button half 132 and second button half 134 also include "half circular" sections 131 and 133 which creates a coupled interaction between these two components. As such, first button half 132 and second button half 134 will rotate together about transverse axis 50 and will not rotate independently. Due to the dimensions, first button half 132 and second button half 134 will be slideable along transverse axis 50, allowing movement between the depressed position and the released position, mentioned above. As will be appreciated, these structures further enhance operation of the locking structures involved.

As also shown in FIG. 6, central joint member 100 includes an internal gear structure 106 which extends around an inner surface of a central opening. When appropriately positioned, internal gear structure 106 will interact with gear members 144 and 148 of first and second button members 132 and 134. This interaction will occur when the button members are seated or in a released position (i.e. held outwardly by force on an internal spring). However, depressing button members 132 and 134 and causing them to slide inwardly to a depressed position will cause disengagement all related gear members. Specifically, internal gear structure 106 will not be engaged with gear members 144 and 148 of button members 132 and 134. That said, first gear structure 142 of first button half 132, and first gear structure 146 of second button half 134, both remain engaged with related teeth in first extension half 122 and second extension half 124. As will be appreciated by those skilled in the art, teeth or gear structures on first button half 132 and second button half 134, in conjunction internal gear structure 106, creates an interference structure which will not allow for rotation of the extension assembly 120 with respect to the central joint member 100 when engaged. That said, when not engaged, rotation is permitted around transverse axis 50, thus allowing extension assembly 120 to be positioned in multiple orientations. Again, when the appropriate buttons are released, the extension assembly 120 will then be locked or secured in place, as desired.

As illustrated in various figures, first extension half 122 and second extension half 124 both include recesses 142 and 144. As will be appreciated by those skilled in the art, the surfaces of extension assembly 120 surrounding recesses 142 and 144 are configured to interact with buttons 74 of slidable collar 70. However, when extension assembly 120 is positioned in a predetermined orientation, posts 74 will be received in these recesses (142, 144), thus allowing movement of slidable collar 70. This movement of slidable collar 70 will allow disengagement of teeth 72, and thus permit rotation of extension assembly 120 about longitudinal axis 30.

Based on the structure above, it can be seen that universal digit 10 is easily adjustable and repositionable by simply actuating buttons 22, 24 and then appropriately aligning extension assembly 120. Again, the internal structures described above provide a positive locking mechanism for universal digit 10 and does not rely upon friction to hold components in place.

Although specific structures have been mentioned above, certain alternative could be used. For example, extension member 120 could be formed as one molded part, thus eliminating the need for two separate components. Further, the structures of the button mechanism could be modified to provide releasable features.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A universal digit, comprising
a barrel portion having a substantially cylindrical shape configured to be aligned with a users' residual digit when in use, the substantially cylindrical shape having a central longitudinal axis;
an extension portion rotatably coupled to the barrel portion, the extension portion having a button mechanism contained therein operable by a user to allow for repositioning of the extension portion relative to the barrel portion when the button mechanism is in a depressed position, the button mechanism further configured to lock the extension portion in a desired orientation by releasing the button mechanism causing the button mechanism to move to a released position;
wherein the extension portion is rotatable about the central longitudinal axis, and is rotatable about a transverse axis, wherein the transverse axis is normal to the longitudinal axis.

2. The universal digit of claim 1 wherein the button mechanism allows rotation about the longitudinal axis and the transverse axis when the button mechanism is depressed, while preventing rotation about the longitudinal axis and the transverse axis when the button mechanism, is released.

3. The universal digit of claim 1 further comprising a central joint member rotatably coupled to the barrel portion and the extension portion, the central joint member configured to accommodate the desired rotation along both the longitudinal axis and the transverse axis, wherein the central joint member has a cylindrical base section at a first end rotatably coupled to the barrel portion, and an extending portion at a second end supporting an aperture extending there through along the transverse axis.

4. The universal digit of claim 3 wherein the button mechanism is partially cylindrical and is situated within the aperture so as to support the rotatable coupling of the extension portion and the central joint member.

5. The universal digit of claim 4 wherein an interior surface of the aperture includes a plurality of teeth positioned thereon, and wherein the button mechanism has a plurality of cooperating teeth on an outer surface thereof, the button mechanism being movable between the depressed position and the released position and wherein the plurality of teeth on the interior surface of the aperture and the plurality of teeth on the button mechanism are engaged when the button mechanism is in the released position and are not engaged when the button mechanism is in the depressed position.

6. The universal digit of claim 1 wherein the button mechanism has a first button member and a second button member which cooperate with one another, the button mechanism being operable by applying a compression force which will move the button mechanism from the released position to the depressed position.

7. The universal digit of claim 6 wherein the first button member and the second button member are moved closer to one another when in the depressed position.

8. The universal digit of claim 7 further comprising a central joint member coupled to the barrel portion and the extension portion, the central joint member configured to accommodate the desired rotation, wherein the central joint member has a cylindrical base section at a first end coupled to the barrel portion, and an extended portion at a second end supporting an aperture extending there through along the transverse axis, and the button mechanism is partially cylindrical and is situated within the aperture so as to support the rotatable coupling of the extension portion and the central joint member, and wherein an interior surface of the aperture includes a plurality of teeth positioned thereon, the button mechanism having a plurality of cooperating teeth on an outer surface thereof, the button mechanism being movable between the depressed position and the released position and wherein the plurality of teeth on the interior surface of the aperture and the plurality of teeth on the button mechanism are engaged when the button mechanism is in the released position and are not engaged when the button mechanism is in the depressed position.

9. The universal digit of claim 8 wherein the extension includes a first extension half and a second extension half, and wherein the first extension half and second extension half have interior recesses so that when they are coupled together, the extension has a slot which is configured to surround the extending portion of the central joint member.

10. The universal digit of claim 9 wherein the first extension half and the second extension half contain the button mechanism when coupled together.

11. A universal digit configured for attachment to a residual digit of a user, comprising:
a substantially cylindrical barrel portion having an attachment end and a joint end, wherein the attachment end is configured to be coupled to the residual digit;
a central joint member rotatably attachable to the joint end of the barrel portion so as to allow rotation of the central joint member about a longitudinal axis which is generally aligned with a cylindrical axis of the barrel portion;
an extension rotatably coupled at a first end to the central joint member so as to allow rotation about a transverse axis, wherein the transverse axis is substantially perpendicular to the longitudinal axis; and a button mechanism cooperating with the extension, the central joint member and the barrel portion, wherein the button mechanism is slidably coupled to the extension and rotatably coupled to the central joint member, the button mechanism movable between a depressed position and a released position, the button mechanism and the central joint member further having cooperating interference structures so that the extension is not rotatable when the button mechanism is in the released position, the button mechanism further having a slidable collar slidably coupled to the central joint member and cooperating with the barrel portion so that rotation of the central hub member around the longitudinal axis is permitted when the slidable collar is in a first position and rotation of the central hub member is prevented when the slidable collar is in a second position.

12. The universal digit of claim 11 wherein the slidable collar has a portion which interacts with the extension, and wherein the slidable collar released to the first position when the extension is in a predetermined orientation, and is held in the second position when the extension is not in the predetermined position.

13. The universal digit of claim 12 wherein the portion of the slidable collar which interacts with the extension is at least one post, and wherein the post is allowed to enter a recess in the extension when the extension is in the predetermined position.

14. The universal digit of claim 11 wherein the button mechanism comprises a first button half and a second button half which slidably engage with one another so that the first button half and the second button half are moved closer to one another when in the depressed position and are farther from one another when in the released position.

15. The universal digit of claim 14 wherein the extension has a first half and a second half, with each of the first half and the second half having a receiving aperture therein, and wherein the first button half and the second button half are in contact with the first extension half and the second extension half respectively, and are positioned with the respective receiving apertures.

16. The universal digit of claim 15 wherein the button mechanism is movable to the released position by applying opposing inward forces to the first button half and the second button half.

17. The universal digit of claim 15 wherein the receiving apertures have teeth on an edge surface thereof, and the first button half and the second button half have cooperating teeth, thereby permitting sliding motion of the first button half and second button half but preventing rotation with respect to the first extension half and the second button half respectively.

* * * * *